United States Patent [19]

Papas

[11] 4,195,131
[45] Mar. 25, 1980

[54] ENVIRONMENTALLY CONTROLLED UNIT

[76] Inventor: Gary R. Papas, 53 E. Rogues Rd., Huntington, N.Y. 11743

[21] Appl. No.: 970,864

[22] Filed: Dec. 18, 1978

Related U.S. Application Data

[63] Continuation of Ser. No. 775,971, Mar. 9, 1977, abandoned.

[51] Int. Cl.² ............................................. C12B 1/00
[52] U.S. Cl. ................................. 435/291; 435/316; 435/313; 435/240; 435/819
[58] Field of Search ........ 195/127, 139, 142, 103.5 M; 350/92, 93, 95

[56] References Cited

U.S. PATENT DOCUMENTS

| | | | |
|---|---|---|---|
| 2,750,328 | 6/1956 | Stimpson et al. | 195/142 |
| 2,865,816 | 12/1958 | Stefanye et al. | 195/142 |
| 3,022,229 | 2/1962 | Heden | 195/142 |
| 3,562,114 | 2/1971 | Steidl et al. | 195/139 |
| 3,743,582 | 7/1973 | Kitai et al. | 195/142 |

Primary Examiner—Alvin E. Tanenholtz
Attorney, Agent, or Firm—Eisenman, Allsopp & Strack

[57] ABSTRACT

An environmentally controlled unit to receive specimens in standard vessels, such as petri-dishes, within a sealable chamber. Passageways are provided through and around this sealable chamber to provide a controlled flow of fluid throughout the chamber and an additional flow of temperature controlled fluid within the unit adjacent to said chamber.

6 Claims, 8 Drawing Figures

ENVIRONMENTALLY CONTROLLED UNIT

This is a continuation of copending application Ser. No. 775,971, filed Mar. 9, 1977, now abandoned.

BACKGROUND OF THE INVENTION

1. Field of the Invention

This invention relates to apparatus for the study of specimens and cultures; and more particularly relates to an environmentally controlled unit within which specimens may be maintained under temperature and other environmental conditions in accordance with the desires of an operator.

The study and handling of live specimens and cultures often requires that the specimens be maintained under strictly controlled environmental conditions. The most critical of these environmental conditions relate to temperature and atmosphere. One is faced with the need for varying the temperature throughout both cool and hot ranges. Atmospherically speaking, it is preferable to have the opportunity of modifying an environment within a thorough range extending from a vacuum to the presentation of the more noxious gases. Indeed, control over the environment of the specimen includes not only control over gaseous environments; but also other fluids including liquids.

Yet another important requirement of an environmentally controlled unit that is desired for optimum flexibility of employment, is its portability and adaptability to use with microscope equipment.

2. Description of the Prior Art

The examination of specimens and cultures with microscopes has led to the development of specimen housing units of varying forms. The petri-dish is a common vessel for containing such specimens and cultures. Supports and bases for such dishes abound. In addition, environmental testing systems including rather cumbersome housings have been developed within which petri-dishes and the like may be positioned. It is also recognized that the base or mounting for the petri-dish should preferably be optically clear so that the unit can be scanned both optically and with various light and other rays.

SUMMARY OF THE INVENTION

The present invention comprises a completely portable environmentally controlled unit that can be mounted with microscopes and that will maintain specimens under environmental conditions controlled both as to fluid content and temperature. This unit will function not merely as a test chamber, but as a dehydrator/concentrator and a metabolic chemical reactor.

An object of the present invention is to provide an improved portable environmentally controlled unit.

Another object of the invention is to provide an environmental test unit having means for introducing and exhausting environmental fluids into a specimen containing chamber.

Another object of the invention is to provide an environmentally controlled unit that will facilitate metabolic rate and chemical process studies of specimens.

Another object of the invention is to provide an environmental test chamber that is heated and/or cooled by passages surrounding a specimen containing aperture.

Yet another object of the invention is to provide an improved environmentally controlled unit utilizing heat conductive material and adapted for extremes of temperature control ranging on both sides of zero degrees Centigrade.

In accordance with a particular embodiment of the invention, there is provided an environmentally controlled unit formed of a heat conductive housing having a chamber extending through and means for sealing the ends of this chamber. A circuitous passage surrounds the chamber and is adapted to receive and exhaust temperature controlled fluids. In addition, passages are provided for supplying and extracting fluids to and from the chamber, in order to control the environment therein.

A more thorough understanding of the invention along with a better appreciation of the objects and novel features thereof, will be available from the following description that has been made in conjunction with the attached drawings.

DESCRIPTION OF THE PREFERRED EMBODIMENT

Figure 1:
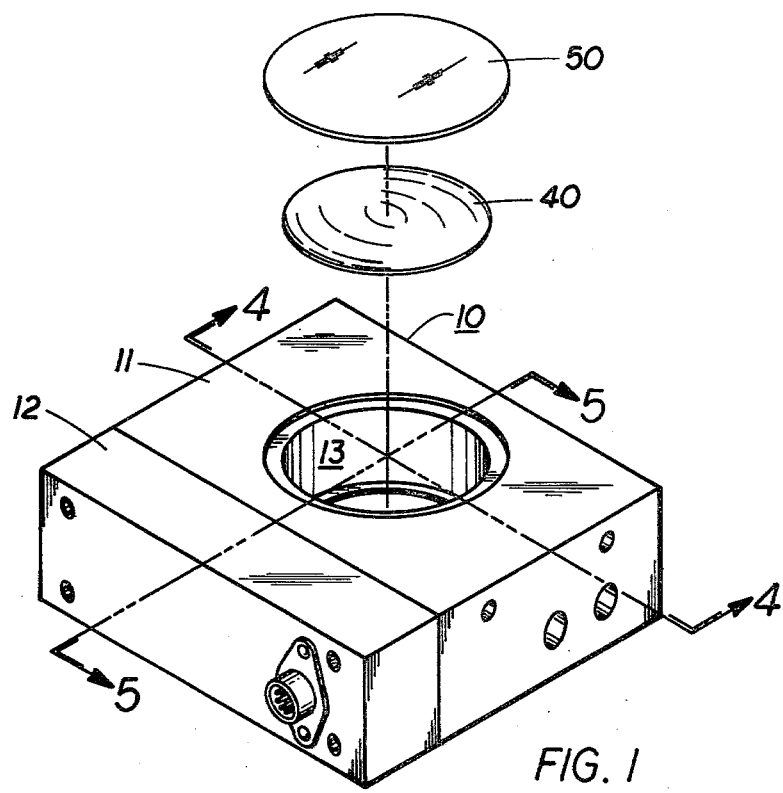
FIG. 1 is a perspective view of an environmentally controlled unit forming an embodiment of the invention.
Figure 2:
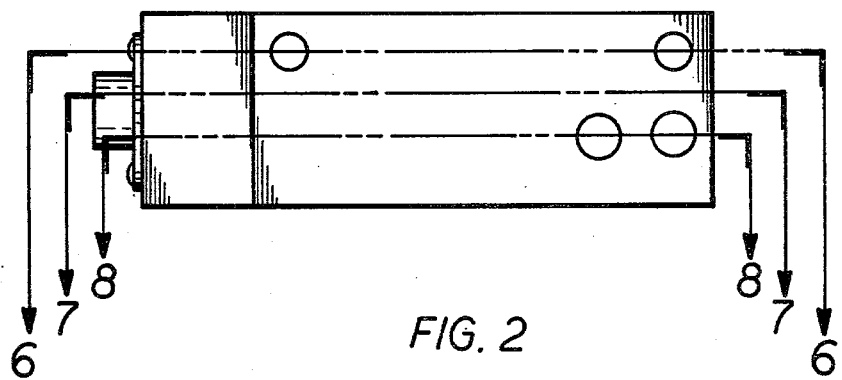
FIG. 2 is a side elevation of the environmentally controlled unit shown in FIG. 1.
Figure 3:
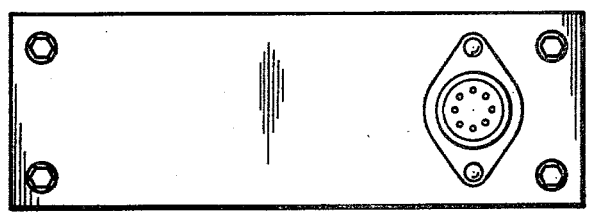
FIG. 3 is a front elevation of the environmentally controlled unit shown in FIG. 1.
Figure 4:
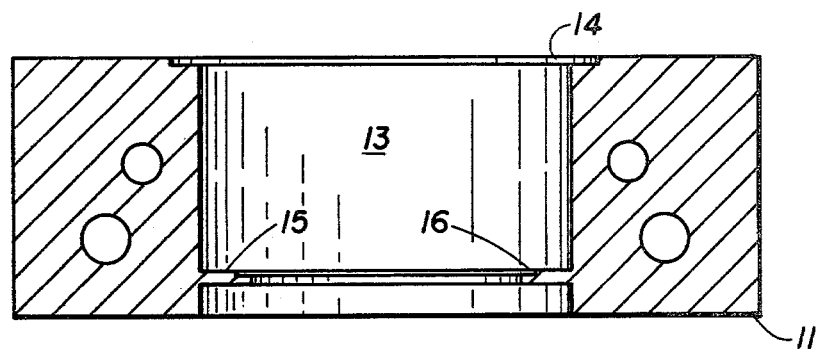
FIG. 4 is a vertical cross-section taken along the lines 4—4 of FIG. 1.
Figure 5:
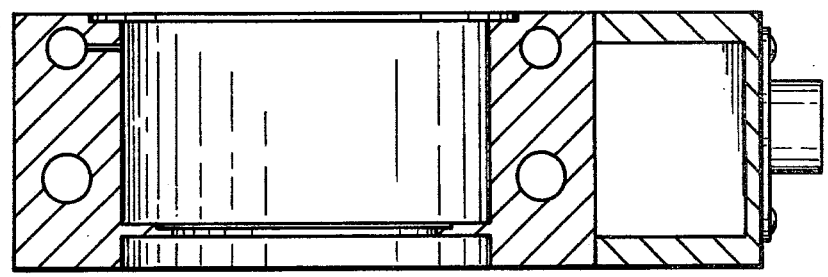
FIG. 5 is a vertical cross-section taken along the lines 5—5 of FIG. 1.

The perspective view of FIG. 1 illustrates an environmentally controlled unit 10. The unit comprises two basic sections 11 and 12 which are assembled preferably as a single block. Section 11 contains the specimen receiving chamber 13 within a substantially solid heat conducting block. As seen clearly in the cross-sectional view of FIG. 4, the chamber contains several shoulders in order to provide suitable mounting for both a specimen containing dish 40 and a flat cover slip 50. The first shoulder 14 may be an indentation in the upper surface of the block 11 and is of sufficient depth and contour to seat a preferably transparent cover slip 50. The second shoulder 15 is disposed closer to the lower portion of the block 11 and projects into the cavity of chamber 13 in order to provide a mounting support for a petri-dish or the like. This shoulder may include a sub-shoulder 16 in order to provide more stable support for the specimen containing dish. The specific location of the second shoulder 15 is determined by the possibility of a downward projection on the specimen containing dish and by the requirement that the temperature and environmental passages within section 11 should control the aperture above this shoulder.

For purposes of discussion, section 11 may be considered to have three basic layers. These layers are illustrated in the horizontal cross-sectional views which make up FIGS. 6, 7 and 8. The upper layer comprises several passageways for the introduction and extraction of a circulating fluid to the test chamber. The second layer may comprise a region for the introduction of electrical heating elements. These elements are located adjacent to the test chamber and due to the heat conductivity of section 11 carefully control the temperature within the chamber. The third layer contains a circuitous passage for the flow of temperature regulating fluid that may be externally controlled in either direction of zero degrees Centigrade. While in the illustrative embodiment the layers have particular elements and forms, variations are obviously possible and sometimes preferable, depending upon specific uses for the environmentally controlled unit.

Figure 6:
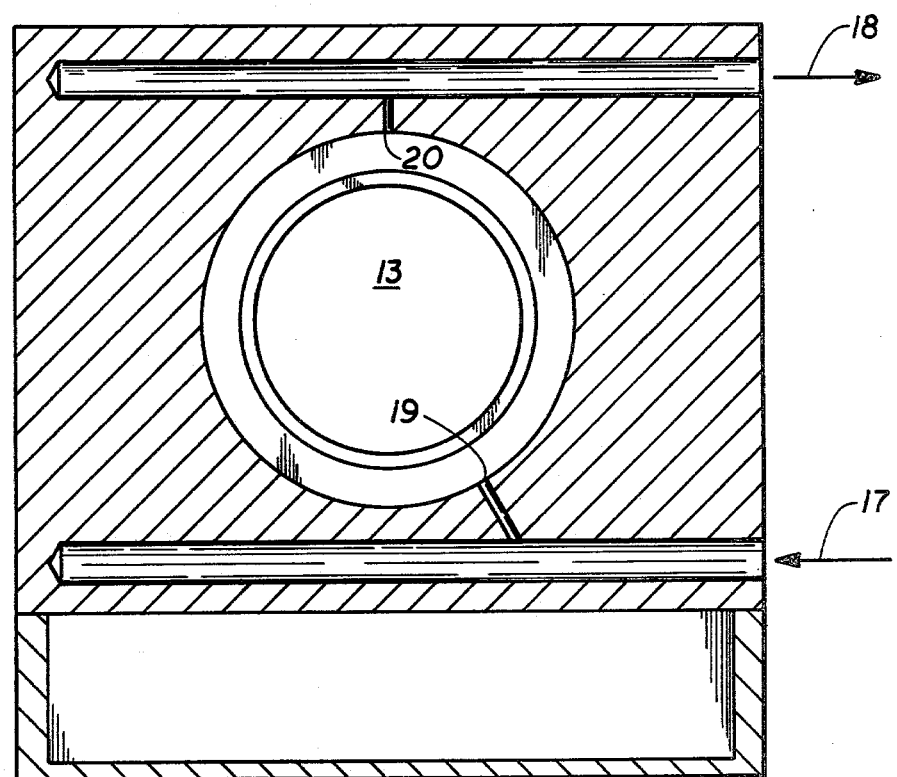
FIG. 6 is a vertical cross-section taken along the lines 6—6 in FIG. 2.

In the illustrated embodiment, the fluid supply layer which controls the atmospheric environment within the chamber, is in the form of the passages 17 and 18 shown in FIG. 6. Interconnecting passages 19 and 20 provide means for fluid entrance from passage 17 into the chamber 13 and for exit therefrom into passage 18. These passages in combination, provide the necessary access to the test chamber for either total exhaust of all gases or for the introduction of any type of gas desired. It will be understood that utilization of this invention and carrying out the test methods of the invention, may include employment of conventional fluid supply equipment that has not been illustrated in the drawings.

Figure 8:
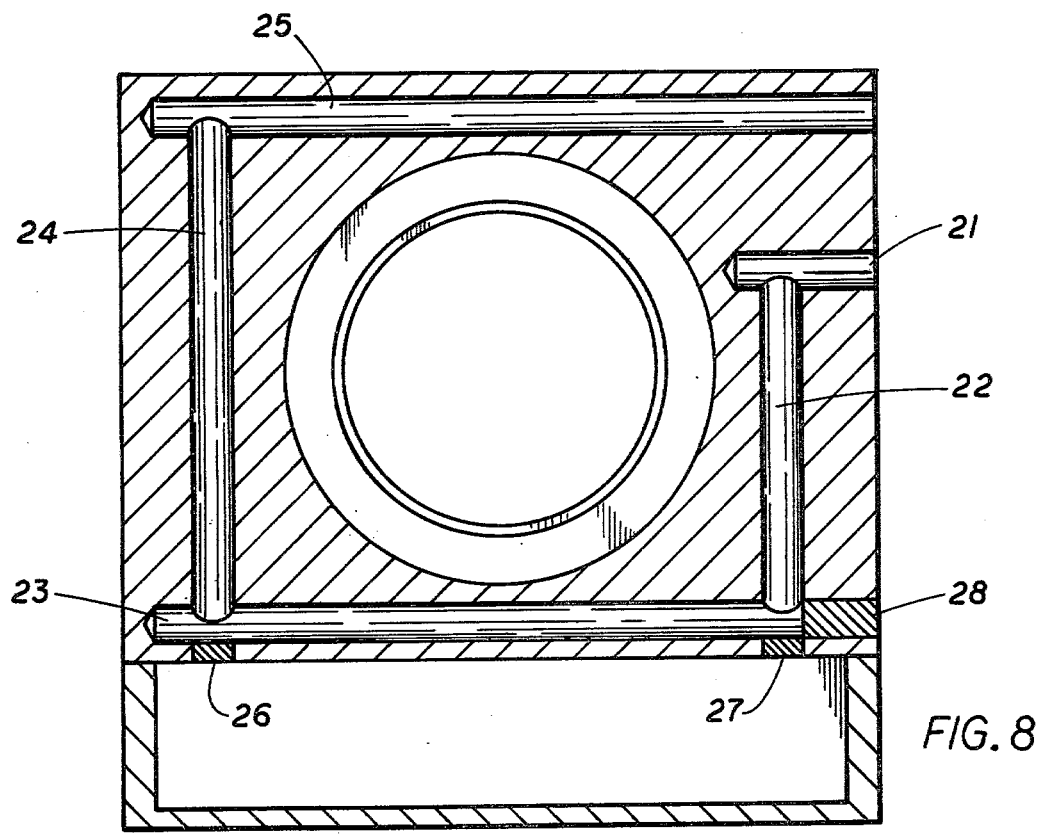
FIG. 8 is a vertical cross-section taken along the lines 8—8 in FIG. 2.

In many instances the temperature of the test chamber will most suitably be controlled by the flow of fluid, either liquid or gaseous, within the passages illustrated in FIG. 8. For convenience, the circuitous passage in this Figure will be seen to have been constructed by the interconnection of five straight passages. These five passages 21, 22, 23, 24 and 25 may be conveniently formed within the solid block forming section 11 by the drilling of holes from both the bottom and right hand sides of the unit, as it is shown positioned in FIG. 8. Where this is done, plugs 26, 27 and 28 may be used to seal the passage openings to the outer surface of the unit. Passages 21-25 do not come in direct contact with chamber 13; however, they do substantially surround the chamber and the temperature of the fluid therein will be quickly conducted to chamber 13. Similarly, if the temperature within chamber 13 is above that of the fluid in passages 21-25, heat will be quickly and effectively extracted by this fluid.

Figure 7:
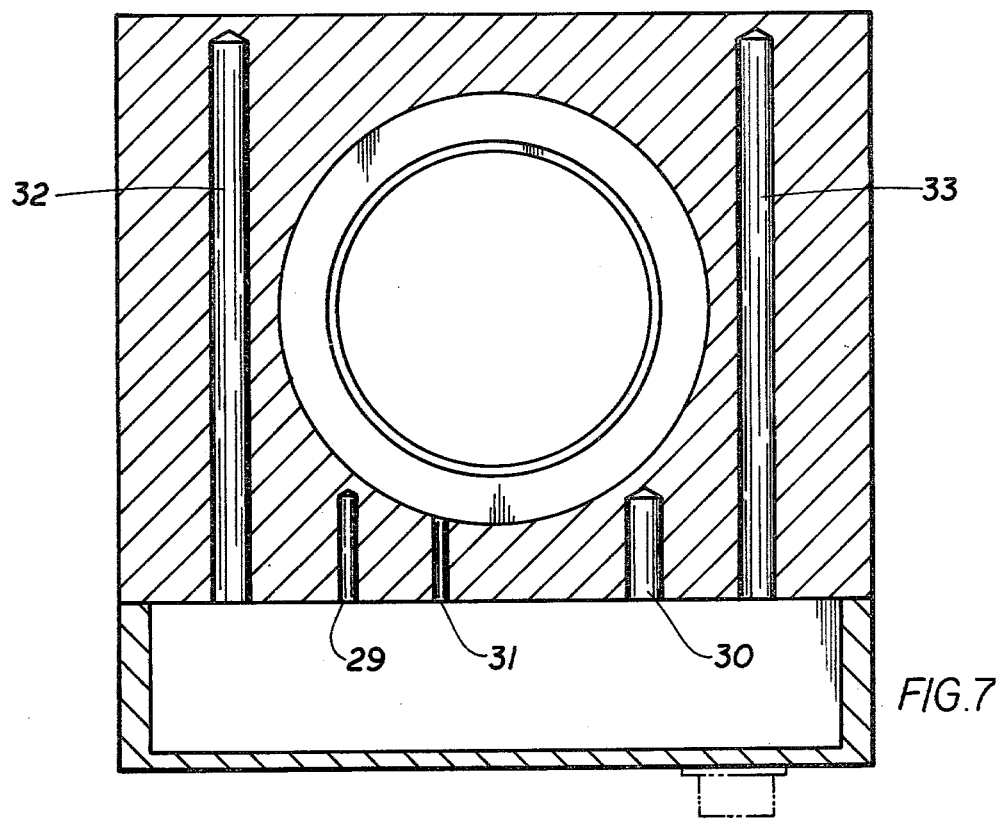
FIG. 7 is a vertical cross-section taken along the lines 7—7 in FIG. 2.

The central layer of the block forming section 11 may be considered as the control portion. As illustrated in FIG. 7, passages may be provided through and into the block in this region, for purposes of sampling the contents of chamber 13 or sensing the temperature of the block itself. For example, temperature sensing means may be inserted at location 29, further temperature sensing means or overshoot protection may be positioned at location 30, and a probe may be inserted at location 31 for direct contact with the contents of chamber 13. In addition, parallel channels 32, 33 are provided on opposed sides of chamber 13 for the receipt of electric heating elements. Calrods, or similar electrical heating elements may be inserted within these channels and may be controlled by known circuitry responsive to suitable sensing elements, to assist in the temperature control of the environment within chamber 13.

Because the sensing and control portions of section 11 emerge from the central region on one side thereof, the control section 12 has been provided with an open chamber that may suitably house electrical or other external elements. In a particular embodiment, the illustrated unit was embodied within the basic dimensions of 4.8 inches by 5.0 inches by 1.7 inches. In this embodiment the test chamber had a diameter of 2.7 inches and was designed to support standard petri-dishes. It will be obvious that these dimensions rendered the unit completely portable and suitable for mounting within most microscope systems for optical analysis of the specimens contained within the chamber.

This invention is ideal for the culture of animal pathogens or hazardous materials. It is a completely enclosed unit that can be loaded in an incubator and sealed insuring a perfectly sterile environment. This test chamber makes it possible to expose cultures to any fluid, gaseous or liquid, uniformly. Tests have indicated that one may subject cultures by means of this test chamber to any temperatures, over an extended period of time, with an accuracy of $+/-0.02$ degrees Centigrade and within a temperature range of $-30$ degrees Centigrade to $+200$ degrees Centigrade.

Any number of chambers comparable to that illustrated herein, may be adapted in a "ganged" arrangement. In this type of arrangement, the passageways may be coupled or positioned so that the fluid will be introduced to control the environment and temperature within adjacent chambers in a variety of preselected fashions. The invention is not limited to the specific physical dimension of the shoulders and can be adapted for various sizes and shapes of vials or petri-dishes. The unit is completely auto-claveable and accordingly can be sterilized easily between uses.

In keeping with the above remarks, it will be understood that the specific embodiment of this invention was not meant to limit the novel features thereof. It will be appreciated that variations and modifications in this embodiment are to be expected from those skilled in the art. All such variations and modifications coming within the scope of the above disclosure and the appended claims, are intended to be covered by these claims.

What is claimed is:

1. An environmentally controlled unit comprising a block of heat conductive material with at least two parallel planar faces and a specimen chamber having two open ends interconnecting said faces, a circuitous passage penetrating said block surrounding said chamber and adapted to receive and exhaust temperature controlled fluid, a first passage penetrating said block to said chamber to supply fluid thereto, a second passage penetrating said block to said chamber to extract fluid therefrom, access to said passages from the outside of said block being provided on wall portions between said faces, a shoulder at one of said ends of said chamber, cover means mounted on said shoulder for sealing said one end, a specimen supporting element, and means for mounting said specimen supporting element to seal the other end of said chamber.

2. An environmentally controlled unit in accordance with claim 1, wherein said first and second passages are on opposite sides of said chamber.

3. An environmentally controlled unit in accordance with claim 1, wherein said circuitous passage lies within a plane that is parallel to a plane containing said first and second passage.

4. An environmentally controlled unit in accordance with claim 1, wherein means are provided for controlling the fluid supplied to said circuitous passage within a temperature range of $-30$ degrees Centigrade to $+200$ degrees Centigrade.

5. An environmentally controlled unit in accordance with claim 1, including electrical heating means disposed on opposite sides of said chamber and adapted to be temperature controlled.

6. An environmentally controlled unit in accordance with claim 1, including sensing means for determining the environmental conditions with said chamber.

* * * * *